(12) United States Patent
Debiemme et al.

(10) Patent No.: US 9,028,670 B2
(45) Date of Patent: May 12, 2015

(54) METHOD FOR PROPORTIONING NITRATES AND/OR NITRITES IN A NEUTRAL MEDIUM

(75) Inventors: Catherine Debiemme, Saint-Maur (FR); Hubert Cachet, Paris (FR); Thi Tuyet Maï Trong Long, Bagnolet (FR); Nizar Aouina, Vincennes (FR)

(73) Assignee: Centre National de la Recherche Scientifique, Paris (FR)

( * ) Notice: Subject to any disclaimer, the term of this patent is extended or adjusted under 35 U.S.C. 154(b) by 375 days.

(21) Appl. No.: 13/508,109

(22) PCT Filed: Nov. 17, 2010

(86) PCT No.: PCT/FR2010/052438
§ 371 (c)(1),
(2), (4) Date: May 4, 2012

(87) PCT Pub. No.: WO2011/061441
PCT Pub. Date: May 26, 2011

(65) Prior Publication Data
US 2012/0217172 A1 Aug. 30, 2012

(30) Foreign Application Priority Data
Nov. 19, 2009 (FR) ...................... 09 58178

(51) Int. Cl.
*G01N 27/38* (2006.01)
*G01N 27/404* (2006.01)
(52) U.S. Cl.
CPC .............. *G01N 27/38* (2013.01); *G01N 27/404* (2013.01)

(58) Field of Classification Search
USPC .............. 204/405, 412, 292; 205/780.5, 781, 205/793.5
See application file for complete search history.

(56) References Cited

PUBLICATIONS

G. Karim-Nezhad, et al. "Copper (hydr)oxide modified copper electrode for electrocatalytic oxidation of hydrazine in alkaline media" Electrochimica Acta, vol. 54, No. 24, Oct. 2009, p. 5721-5726.*
International Search Report dated Apr. 21, 2011.

* cited by examiner

Primary Examiner — J. Christopher Ball
(74) Attorney, Agent, or Firm — Sofer & Haroun, LLP

(57) ABSTRACT

The present invention relates to a method for proportioning nitrate and/or nitrite ions in a solution using a copper electrode, said method being characterized in that it is carried out in constant potential mode and moreover in that it includes the steps of: i. applying a first potential to the copper electrode so as to reduce the copper oxides present on the surface of the metal copper electrode; ii. applying a second potential to the copper electrode so as to oxidize the metal copper formed in Step i into cupric ions; iii. applying a third potential to the copper electrode so as to reduce the copper oxides possibly formed in Step ii. Steps i through iii being carried out in a support electrolyte; and iv. proportioning the nitrate and/or nitrite ions of a solution to be analyzed by means of immersing the copper electrode, obtained in Step iii, in said solution to be analyzed while applying a fourth potential to the copper electrode so as to reduce the nitrate and/or nitrite ions, the support electrolyte of Steps i through iii, and the solution to be analyzed in Step iv, having a substantially neutral pH.

9 Claims, 4 Drawing Sheets

METHOD FOR PROPORTIONING NITRATES AND/OR NITRITES IN A NEUTRAL MEDIUM

RELATED APPLICATIONS

This application is a National Phase application of PCT/FR2010/052438, tiled on Nov. 17, 2010, which in turn claims the benefit of priority from French Patent Application No. 09 58178 filed on Nov. 19, 2009, the entirety of which are incorporated herein by reference.

BACKGROUND

1. Field of the Invention

The present invention relates to a method for titrating nitrate and/or nitrite ions in solution at a substantially neutral pH.

2. Description of Related Art

It applies, typically but not exclusively, to the use of a copper electrode for the potentiostatic titration of nitrate and/or nitrite ions in an aqueous medium having a substantially neutral pH.

Many methods for quantitatively determining nitrate and/or nitrite ions are known, in particular at a highly acidic pH. Mention may be made, for example, of the document entitled "*The effect of surface preparation of a copper electrode on the reduction of nitrate ions*" by Aljaz Coh and Boris Pihlar (Acta Chimica Slovenia, 43/1/1996, pp. 5-12). This document exhibits a method for the titration of nitrate ions using a copper electrode.

This titration method comprises a first stage which consists in applying a potential of between 0 and 0.2 V vs. Ag/AgCl to the copper electrode for a predetermined time, so as to oxidize the metal copper of said electrode and thus form a layer of copper oxide, and a second stage which consists in titrating, by reduction, the nitrate ions by scanning the potential applied to the copper electrode ("potentiodynamic mode" titration), the first and second stages being carried out in a highly acidic medium in a solution of the 0.1 M $HClO_4$/0.9 M $NaClO_4$ type. Furthermore, even if this document mentions that a layer of copper oxide is formed, it is difficult to envisage that the layer of copper oxide can exist in a highly acidic medium.

The plot of the curve of the intensity as a function of the potential applied to the copper electrode then makes it possible to identify the current peak due to the reduction of nitrate ions to give $NH_4^+$ ions and to thus deduce therefrom the concentration of nitrate ions by calibration in the acidified aqueous medium.

In addition, according to this method, it is preferable to add $Cu^{2+}$ ions to the acidic medium to be analyzed in order to catalyze the reduction of the nitrate ions during the titration stage.

However, during the implementation of this titration method in potentiodynamic mode, that is to say with gradual scanning of the potential applied to the copper electrode, a gradual decrease in the current measured is observed, which decrease is due to poisoning of the electrode, and it is thus impossible to carry out reproducible measurements one after the other.

Furthermore, the concentration of nitrate ions cannot be measured in a technically simple way since the variation in the potential with a given rate, in potentiodynamic mode, involves the use of relatively complex electronic equipment.

In addition, by this method, it is not possible to titrate the nitrate ions in an unmodified natural medium as it is necessary to add a strong acid, indeed even $Cu^{2+}$ ions, to the medium to be analyzed.

Finally, the measurements in an acidic medium are limited since they do not make it possible to observe the reduction of the nitrite ions. This is because, when the medium is acidified, the nitrite ions initially present in the medium are in the form of nitrous acid ($HNO_2$, pKa=3.3). Nitrous acid is unstable and then disproportionates to give nitrates and NO.

OBJECTS AND SUMMARY

The aim of the present invention is to overcome the disadvantages of the techniques of the prior art by providing in particular a method for the simple and direct titration of nitrate and/or nitrite ions which makes it possible to guarantee reproducible and reliable measurements, whatever the number of titrations to be carried out, without it being necessary to add any additive to the solution to be analyzed, in particular for modifying the pH thereof.

A subject matter of the present invention is a method for titrating nitrate and/or nitrite ions in solution using a copper electrode, characterized in that it is carried out in potentiostatic mode and in that it comprises the stages consisting in:

i. applying a first potential to the copper electrode, so as to reduce the copper oxides present at the surface of the electrode to copper metal $Cu^0$), ii. applying a second potential to the copper electrode, so as to oxidize the copper metal formed in stage i to cupric ($Cu^{2+}$) ions, it possibly being possible for copper oxides to be formed during stage ii, iii. applying a third potential to the copper electrode, so as to reduce the copper oxides possibly formed in stage ii, stages i to iii being carried out by immersion of the copper electrode in a supporting electrolyte, the supporting electrolyte preferably being an aqueous supporting electrolyte, and iv. titrating the nitrate and/or nitrite ions of a solution to be analyzed, by immersion of the copper electrode obtained in stage iii in said solution to be analyzed, a fourth potential being applied to the copper electrode, so as to reduce the nitrate and/or nitrite ions, the supporting electrolyte of stages i to iii, and the solution to be analyzed of stage iv, having a substantially neutral pH.

The term "substantially neutral" is understood to mean a solution (or an electrolyte) having a pH close to neutrality, that is to say which can range from 5 to 9 and is preferably approximately equal to 7. By way of example, the solution to be analyzed can be an aqueous medium, such as natural water or wastewater.

Thus, the titration method according to the invention, which is an electrochemical method, advantageously makes it possible to carry out the direct titration of the nitrate and/or nitrite ions possibly present in any solution, without it being necessary to add additional compounds (or additives) to said solution, such as, for example, a strong acid, in order to lower the pH thereof, cupric ($Cu^{2+}$) ions, in order to catalyze the reduction of the nitrate ions during the titration stage, buffer solutions, and the like.

The expression "copper electrode" is understood to mean an "unalloyed" copper electrode composed solely of copper, it being possible for the copper to be bulk or electrodeposited. Of course, the copper electrode may comprise inevitable impurities, such as, for example, other metal elements. In this case, the copper electrode is at least 99.9% by weight composed of copper, the remainder being said inevitable impurities.

Stages i to iii are "conditioning stages" for the electrode, prior to the titration stage iv proper. These conditioning stages, which consist in applying, to the copper electrode, a sequence of three successive potentials in potentiostatic mode, advantageously make it possible to obtain a surface of the electrode essentially composed of copper in the 0 oxidation state and thus devoid of copper oxide, in order have a constant and reproducible active surface.

These conditioning stages i to iii are carried out in the supporting electrolyte, it advantageously being possible for the latter to be the solution to be analyzed of stage iv. In this case, reference is made to conditioning and titration carried out in situ, in the same solution having a substantially neutral pH.

The titration stage iv is a "potentiostatic" (or "amperometric") titration. This type of titration is well known and consists in measuring the intensity of the current, which is a function of the concentration of nitrate and/or nitrite ions, at a given potential (i.e., fourth potential).

The potentiostatic mode used in stages i to iv advantageously makes it possible to apply a constant potential for a predetermined time, which is technically much simpler than to vary this potential with a given rate, such as in potentiodynamic mode.

By virtue of the invention, the concentration of nitrate and/or nitrite ions present in the solution to be analyzed is proportional to the intensity measured at the potential (i.e., fourth potential) applied to the conditioned copper electrode. This potentiostatic titration thus makes it possible to easily obtain the concentration of nitrate and/or nitrite ions. More particularly, at a given fourth potential, either the concentration of nitrate ions or the concentration of nitrate ions and nitrite ions is obtained.

The potentiostatic titration according to the invention is thus very different from potentiodynamic titration (cyclic voltammetry), in which the potential applied to the copper electrode varies as a function of the time (potential scanning).

In the titration method of the invention, the first potential makes it possible to reduce copper oxides of the CuO and/or $Cu_2O$ type to copper metal, said copper oxides originating in particular from the oxidation of the copper metal by atmospheric oxygen. The first potential is thus of cathodic type; it must allow the reduction of all the copper oxides.

Typically, it can be less than or equal to −0.85 V with respect to a reference electrode of the saturated calomel electrode type (i.e., calomel electrode saturated with KCl), denoted in the continuation of the description by "SCE", and preferably equal to −1.15 V/SCE. Ideally, the duration of application of the first potential can be at least a few seconds, for example between 20 and 30 seconds.

The electrochemical half equations for the reduction of the copper oxides are as follows:

$$CuO+2e^-+H_2 \rightarrow Cu^0+2OH^-$$

$$Cu_2O+2e^-+H_2O \rightarrow 2Cu^0+2OH^-$$

The second potential makes it possible to oxidize the copper metal formed in stage i to give cupric ($Cu^{2+}$) ions. The second potential is thus of anodic type.

Typically, the second potential can be greater than the rest potential of the copper electrode, in particular greater by from 5 to 200 mV, with respect to said rest potential, and preferably greater by 5 to 100 mV, with respect to said rest potential.

A second potential greater by more than 200 mV, with respect to the rest potential, would not necessarily be acceptable owing to the fact that it might bring about excessively great dissolution of the copper metal and, for this reason, the active surface of the electrode would become nonuniform, as explained below.

The rest potential corresponds to the open circuit potential or, in other words, to the "natural" potential measured when the copper electrode is not subjected to the application of any potential. This rest potential is thus conventionally measured between the copper electrode and a reference electrode, for example of SCE type, without any potential being applied between these two electrodes. By way of example, the rest potential of the copper electrode can be approximately equal to −0.10 V/SCE.

More particularly, when the open circuit potential is −0.100 V/SCE, the second potential can be greater than or equal to −0.095 V/SCE and less than or equal to 0.100 V/SCE, and preferably less than or equal to 0.000 V/SCE.

Ideally, the duration of application of the second potential can be at least a few seconds, for example between 20 and 30 seconds.

The electrochemical half equation of the oxidation of the copper metal is as follows:

$$Cu^0 \rightarrow Cu^{2+}+2e^-$$

During the application of the second potential, copper oxides, such as, for example, CuO and/or $Cu_2O$, may possibly be formed.

The reduction of the copper oxides in stage i can result in the formation of divided copper (or noncompact copper) on the surface of the copper electrode, which results in a surface nonuniformity (surface roughness) and an increase in the active surface of said electrode. For this reason, stage ii makes it possible to guarantee measurements which are reproducible one after the other, guaranteeing an active surface which remains uniform and homogeneous (smooth surface) as the titrations are carried out.

The third potential makes it possible, for its part, to reduce the copper oxides possibly formed during stage ii. The third potential is thus of cathodic type. It can be less than or equal to −0.85 V/SCE and preferably equal to −1.15 V/SCE.

Ideally, the duration of application of the third potential can be at least a few seconds, for example between 20 and 30 seconds.

Thus, the combination of stages i, ii and iii makes it possible to obtain a copper electrode having a surface which has been conditioned and which then makes it possible, during the titration of the nitrate and/or nitrite ions in stage iv, to measure a reduction current which is reproducible and proportional to the concentration of nitrate and/or nitrite ions in the solution to be analyzed.

The fourth potential makes it possible to reduce the nitrate and/or nitrite ions in order to titrate them (i.e., to detect quantitatively). This fourth potential is thus of cathodic type.

The term "nitrate and/or nitrite ions" of the invention more particularly denotes either nitrate ions or nitrate ions and nitrite ions.

According to a first alternative form, the fourth potential is equal to approximately −0.9 V/SCE, in order to carry out only the reduction of the nitrate ions according to the following equation:

$$NO_3^-+2e^-+H_2O \rightarrow NO_2^-+2OH^-$$

At this potential (−0.9 V/SCE), the nitrate ions are thus reduced to nitrite ions.

According to a second alternative form, the fourth potential is equal to approximately −1.1 V/SCE and makes it possible to carry out both the reduction of the nitrate ions and that of the nitrite ions, according to the following equations:

The content of nitrite ions is thus easily obtained by difference between the intensity of the currents obtained at −0.9 V/SCE (cf., reduction of the nitrate ions) and at −1.1 V/SCE (reduction of the nitrite ions and nitrate ions).

According to a third alternative form, the fourth potential comprises the application of the potential at approximately −0.9 V/SCE, followed by the application of the potential at approximately −1.1 V/SCE.

Ideally, the duration of application of the fourth potential can be at least a few seconds, for example between 20 and 30 seconds.

Of course, a person skilled in the art will easily understand that all the stages can be carried out only in the presence, in addition to the copper electrode, of a reference electrode, for example of SCE type, of a counterelectrode, for example made of platinum or of stainless steel, and of an electronic measurement device, together forming an electrochemical sensor.

In a particularly preferred embodiment, stages i to iii are repeated before each titration stage iv, thus making it possible to carry out continuous titrations while ensuring the reproducibility of the measurements and while keeping unchanged the performances of the copper electrode.

In addition, in a very specific embodiment, the titration method of the invention additionally comprises a stage v subsequent to the titration stage iv, said stage v consisting in maintaining the copper electrode at a fifth potential, said fifth potential being lower than the rest potential of the copper electrode, so as to prevent the copper electrode from oxidizing when the latter is no longer used for said titration for a given period.

The fifth potential advantageously makes it possible to prevent the copper from oxidizing (i.e., from corroding), which might result in the formation of a significant film of copper oxide at the surface of the copper electrode, thus preventing reproducible measurements from being obtained.

As mentioned above, the rest potential of the copper electrode (or open circuit potential) can, for example, be approximately equal to −0.10 V/SCE.

Another subject matter of the invention is a copper electrode conditioned by stages i to iii of the titration method as defined in the present invention. Said copper electrode is characterized in that its surface is essentially composed of copper in the 0 oxidation state (Cu(0)), that is to say copper in the metal form.

The term "essentially" is understood to mean a content as atomic percentage (at. %) of copper in the 0 oxidation state which is greater than 80 at. %, and preferably greater than 90 at. %, with respect to the sum of the contents in at. % of all the constituents comprising at least one metal element present at the surface of the copper electrode. The group of said constituents comprises, of course, copper in the metal form (Cu (0)) and can additionally comprise copper in the +I oxidation state (Cu(I)) and/or copper in the +II oxidation state (Cu(II)).

More particularly, the surface of the copper electrode comprises less than 10 at. % of copper oxide(s), preferably less than 5 at. % of copper oxide(s).

In a preferred embodiment, the surface of the copper electrode does not comprise copper oxide and, particularly preferably, the surface of the copper electrode is composed only of copper in the 0 oxidation state.

Finally, another subject matter of the invention is the use of such a conditioned copper electrode for the titration of nitrate and/or nitrite ions in a solution having a substantially neutral pH, said titration being carried out in potentiostatic mode.

BRIEF DESCRIPTION OF THE DRAWINGS

Other characteristics and advantages of the present invention will become apparent in the light of the description of a nonlimiting example of the titration method according to the invention, made with reference to the annotated figures, in which.

DETAILED DESCRIPTION

Examples

Figure 1:
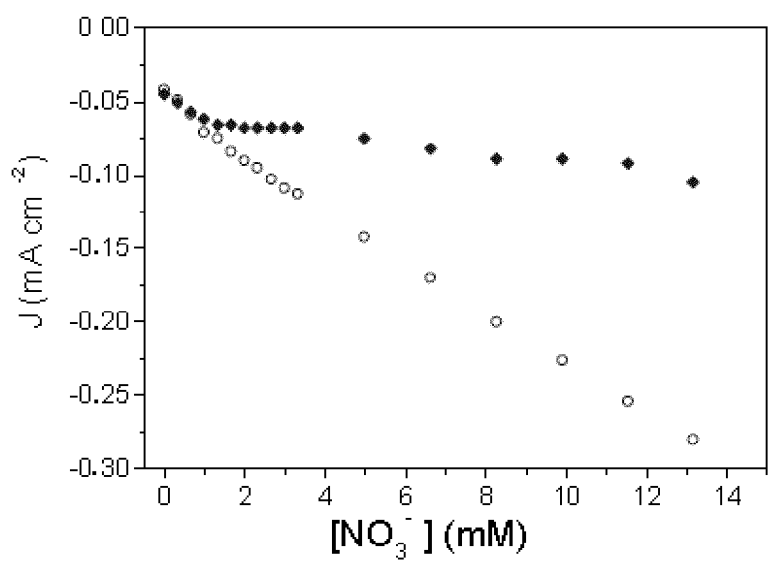
FIG. 1 represents two titration curves for currents recorded at a potential −0.9 V/SCE as a function of the concentration of nitrate ions in a 2 mM Na$_2$SO$_4$ solution, with and without conditioning of the copper electrode.

In order to obtain the curves of FIG. 1, measurements of the current density (J) (i.e., current measured per unit of surface area of the copper electrode) as a function of the concentration of nitrate ions were made.

To do this, a copper electrode was immersed in a 2 mM aqueous Na$_2$SO$_4$ solution to which had been successively added predetermined amounts of a sodium nitrate solution in order to increase the concentration of nitrate ions in the solution analyzed.

According to a first test, the copper electrode is directly polarized in the aqueous solution, at a potential of −0.9 V/SCE. This potential makes it possible to reduce the nitrate ions to nitrite ions. The curve obtained is that represented by the sequence of points "♦".

According to a second test, the copper electrode is first of all conditioned. In particular, it is conditioned before the first addition of a predetermined amount of said sodium nitrate solution and also after each addition of each predetermined amount of said sodium nitrate solution to the aqueous solution, the conditioning being carried out according to stages i to iii of the invention at the following successive potentials:

a first potential of −1.15 V/SCE is applied (stage i) for approximately 30 seconds, a second potential of 0.05 V/SCE is applied (stage for approximately 30 seconds, and a third potential of −1.15 V/SCE is applied (stage iii for approximately 30 seconds.

The electrode thus conditioned is then polarized at a fourth potential (stage iv) of −0.9 V/SCE for approximately 30 seconds.

The curve obtained is that represented by the sequence of points "O".

When the copper electrode is conditioned between each measurement, it is clearly observed in FIG. 1 that the response obtained is proportional to the content of nitrate ions in the solution analyzed. This is because the relationship of the current density as a function of the concentration of nitrate ions is linear. This is not the case when the electrode is not conditioned between each measurement.

Figure 2:
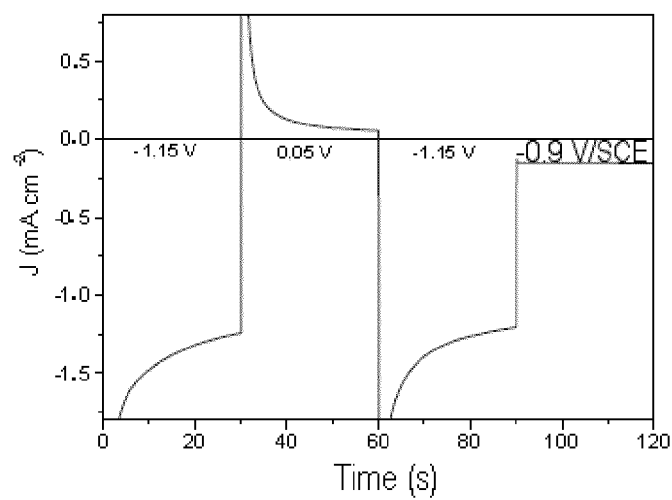
FIG. 2 represents the current density as a function of the time for the titration of the nitrate ions according to the invention.

FIG. 2 represents the current density as a function of the time for the titration of the nitrate ions according to the invention with a given aqueous solution.

The copper electrode is immersed in an aqueous solution comprising 0.002 M of $Na_2SO_4$ and 0.005 M of $NaNO_3$.

The potential sequence applied for the conditioning of the electrode (stages i, ii and iii) and for the titration of the nitrate ions (stage iv) is identical to that mentioned for FIG. 1.

Figure 3:
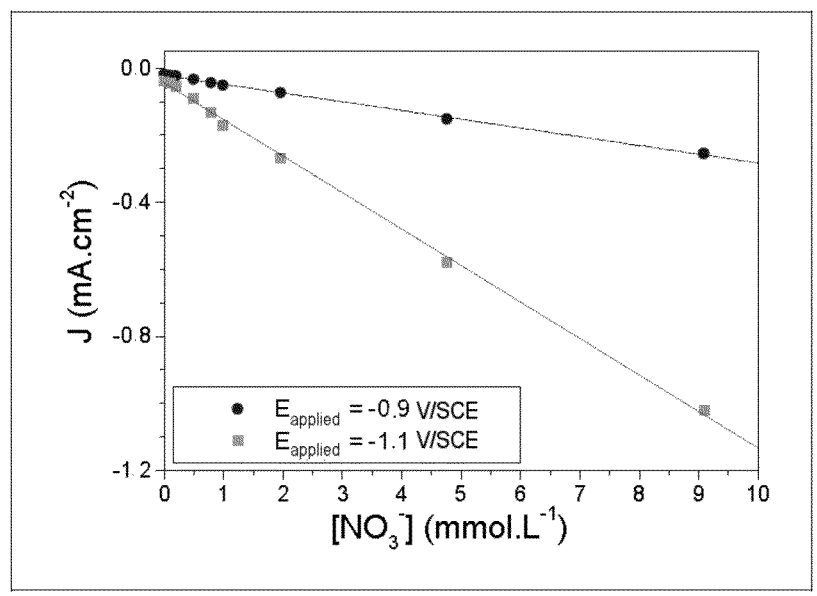
FIG. 3 represents the variation in the current density as a function of the concentration of nitrate ions after conditioning of the copper electrode at a potential of −0.9 V/SCE and of −1.1 V/SCE.

FIG. 3 represents the variation in the current density as a function of the concentration of nitrate ions after conditioning the electrode by applying the potential sequence as mentioned in FIG. 1. The titration of the nitrate ions is carried out, on the one hand, at a potential of −0.9 V/SCE and, on the other hand, at a potential of −1.1 V/SCE.

To do this, a copper electrode was immersed in a 2 mM aqueous $Na_2SO_4$ solution to which were added successively predetermined amounts of a sodium nitrate solution in order to increase the concentration of nitrate ions in the solution analyzed.

FIG. 3 makes it possible to observe the linearity in the relationship as a function of the concentration of nitrate ions at −0.9 V/SCE and at −1.1 V/SCE.

Figure 4:
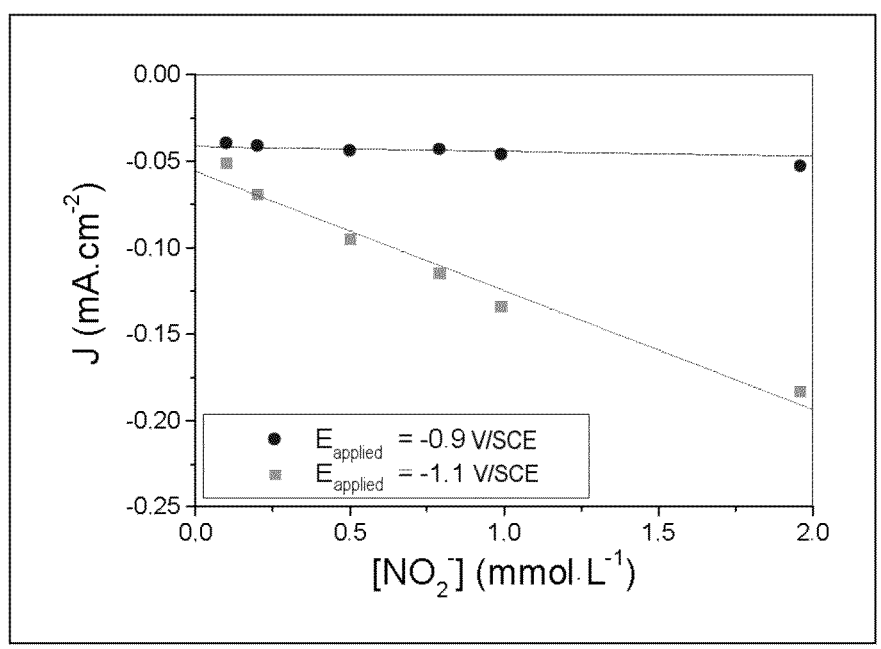
FIG. 4 represents the variation in the current density as a function of the concentration of nitrite ions after conditioning of the copper electrode at a potential of −0.9 V/SCE and −1.1 V/SCE.

FIG. 4 represents the variation in the current density as a function of the concentration of nitrite ions after conditioning the electrode by applying the potential sequence as mentioned in FIG. 1. The titration of the nitrite ions is carried out at a potential of −1.1 V/SCE. In addition, it is confirmed that, at −0.9 V/SCE, the current density does not vary.

To do this, a copper electrode was immersed in a 2 mM aqueous $Na_2SO_4$ solution to which were successively added predetermined amounts of a sodium nitrite solution in order to increase the concentration of nitrite ions in the solution analyzed.

FIG. 4 makes it possible to observe the linearity in the relationship J directly as a function of the concentration of nitrite $NO_2^-$ ions at −1.1 V/SCE since the aqueous solution does not comprise nitrate ions. In the contrary case, when the aqueous solution to be analyzed comprises nitrate ions, the concentration of nitrite ions can easily be calculated using the following relationship: $J(NO_2^-)=J(-1.1\ V/SCE)-J(-0.9\ V/SCE)$.

Consequently, the titration method according to the invention, including a conditioning of the copper electrode prior to the titration or prior to each titration, is a method which is simple to employ and which makes it possible to have reproducible measurements of the concentration of nitrate and/or nitrite ions, whatever the solution of substantially neutral pH considered.

The invention claimed is:

1. A method for titrating nitrate and/or nitrite ions in solution using a copper electrode, said method being carried out in potentiostatic mode and in including the stages consisting in:
   i. applying a first potential to the copper electrode, so as to reduce the copper oxides present at the surface of the electrode to copper metal,
   ii. applying a second potential to the copper electrode, so as to oxidize the copper metal formed in stage i to give cupric ions,
   iii. applying a third potential to the copper electrode, so as to reduce the copper oxides possibly formed in stage ii, stages i to iii being carried out in a supporting electrolyte, and
   iv. titrating the nitrate and/or nitrite ions of a solution to be analyzed, by immersion of the copper electrode obtained in stage iii in said solution to be analyzed, a fourth potential being applied to the copper electrode so as to reduce the nitrate and/or nitrite ions,
   the supporting electrolyte of stages i to iii and the solution to be analyzed of stage iv having a substantially neutral pH.

2. The method as claimed in claim 1, wherein the supporting electrolyte of stages i to iii is the solution to be analyzed of stage iv.

3. The method as claimed in claim 1, wherein the first potential is less than or equal to −0.85 V/SCE.

4. The method as claimed in claim 1, wherein the second potential is greater than the rest potential of the copper electrode.

5. The method as claimed in claim 1, wherein the third potential is less than or equal to −0.85 V/SCE.

6. The method as claimed in claim 1, wherein the fourth potential is equal to approximately −0.9 V/SCE.

7. The method as claimed in claim 1, wherein the fourth potential is equal to approximately −1.1 V/SCE.

8. The method as claimed in claim 1, wherein stages i to iii are repeated before each titration stage iv.

9. The method as claimed in claim 1, wherein said method additionally comprises a stage v subsequent to the titration stage iv, said stage v consisting in maintaining the copper electrode at a fifth potential, said fifth potential being lower than the rest potential of the copper electrode, so as to prevent the copper electrode from oxidizing when the latter is no longer used for said titration for a given period.

* * * * *